United States Patent [19]
Broekhuis

[11] 4,455,447
[45] Jun. 19, 1984

[54] PROCESS FOR UPGRADING HYDROCARBON STREAMS COMPRISING CONJUGATED DIOLEFINS

[75] Inventor: Antonius A. Broekhuis, Amsterdam, Netherlands

[73] Assignee: Shell Oil Company, Houston, Tex.

[21] Appl. No.: 479,289

[22] Filed: Mar. 28, 1983

[30] Foreign Application Priority Data

May 18, 1982 [NL] Netherlands ............... 8214486

[51] Int. Cl.$^3$ ............................................. C07C 7/10
[52] U.S. Cl. ..................... 585/853; 585/861; 585/810; 208/331
[58] Field of Search ............... 585/853, 860, 861, 810; 208/331, 289, 283, 284

[56] References Cited

U.S. PATENT DOCUMENTS

| | | | |
|---|---|---|---|
| 2,389,973 | 4/1946 | Soday | 585/810 |
| 2,423,389 | 7/1947 | Jordan | 585/853 |
| 3,284,339 | 11/1966 | Begley et al. | 208/331 |
| 3,285,989 | 11/1966 | Wolfe et al. | 585/854 |
| 3,792,105 | 2/1974 | Siegmann | 585/810 |
| 4,060,567 | 11/1977 | Tazuma et al. | 585/853 |

FOREIGN PATENT DOCUMENTS 602486  4/1978  U.S.S.R. ............... 585/860

Primary Examiner—Delbert E. Gantz
Assistant Examiner—A. Pal
Attorney, Agent, or Firm—Ronald R. Reper

[57] ABSTRACT

Process for the upgrading of hydrocarbons comprising conjugated diolefins using a dispersion of an alkali(ne earth) metal, characterized in that the upgrading is carried out in the presence of an aliphatic amine having at least one primary amine group.

11 Claims, No Drawings

PROCESS FOR UPGRADING HYDROCARBON STREAMS COMPRISING CONJUGATED DIOLEFINS

BACKGROUND OF THE INVENTION

The present invention relates to a process for the upgrading of hydrocarbons or hydrocarbon streams comprising conjugated diolefins.

Conjugated diolefins such as butadiene, isoprene and the piperylenes are valuable starting materials for various chemical processes, in particular polymerization processes. They are normally obtained by thermal or catalytic cracking processes using naphtha or gas oil as feedstock. The conjugated dienes are normally present in admixture with allenes, alkynes and the corresponding (cyclo) mono-olefins and alkanes, or, when appropriate, as cis-trans mixtures which also may contain allenes, alkynes and the corresponding (cyclo) mono-olefins and alkanes. For polymerization purposes high quality grade conjugated dienes are required. The product mixtures obtained by the cracking process are therefore normally subjected to a further sophisticated treatment (e.g., a distillation-extraction process) so as to warrant good quality products.

It would constitute a considerable advantage when mixtures containing conjugated diolefins, also comprising mono-olefins and alkanes, could be upgraded by a straightforward, low-temperature treatment. It should be noted that the expression "upgrading" as used herein both refers to the partial or total removal of unwanted allenes and alkynes, thus improving the purity of the starting material, as well as to increasing the amount of the more readily polymerizable isomer, thus enlarging the concentration of the desired isomer in the starting material.

Various methods have already been suggested in the art. It is possible, for instance, to subject the hydrocarbon stream comprising conjugated diolefins together with allenic and alkynic impurities (e.g. $C_4$-streams ex naphtha cracker) to a hydrogenation treatment to remove such impurities. However, such hydrogenation treatment suffers from a low selectivity in the reduction of the allenes and alkynes since 1,3-diolefins are substantially reduced as well. A distillation treatment would still be required prior to the hydrogenation treatment in order to keep losses in conjugated diolefins within reasonable limits.

The use of sodium to remove impurities has been widely reported in the literature. Much research has been devoted to the upgrading of, in particular, isoprene using sodium and a polymerization inhibitor (e.g. U.S. Pat. Nos. 2,413,254 and 2,398,810), (supported) alkali-amides (e.g. U.S. Pat. Nos. 3,166,605 and 4,060,567) or a sodium dispersion at a discrete higher temperature (German Offenlegungsschrift No. 2,252,846).

It was found, however, that the use of sodium is insufficient with respect to the partial, let alone total removal of allenic impurities without causing unwanted losses of 1,3-dienes, whereas alkynic impurities such as butyne-1 and vinyl-acetylene can be removed easily from 1,3-butadiene using a conventional sodium dispersion.

Surprisingly, it has now been found that allenic impurities can be removed from conjugated dienes by treating such compounds with a dispersion of an alkali(ne earth) metal in the presence of an aliphatic amine having at least one primary amine group. It has further been found that the treatment as described hereinbefore results in an increase in the amount of the trans-isomer of an appropriate conjugated diene which has at least two geometric isomeric forms, starting from all-cis or from a cis/trans mixture.

SUMMARY OF THE INVENTION

The present invention therefore relates to a process for upgrading of hydrocarbons comprising conjugated diolefins using a dispersion of an alkali(ne earth) metal in the presence of an aliphatic amine having at least one primary amine group.

DESCRIPTION OF PREFERRED EMBODIMENTS

One particular aspect of the present invention relates to a process wherein hydrocarbon streams comprising conjugated diolefins containing allenes and possibly acetylenic compounds are treated with a dispersion of an alkali(ne earth) metal in a hydrocarbon also containing an aliphatic amine having at least one primary amine group.

Preferably, the present invention relates to a process wherein hydrocarbon streams containing one or more $C_4$-$C_8$ conjugated diolefins, in particular butadiene, are treated with a dispersion of an alkali(ne earth) metal in a hydrocarbon also containing an aliphatic amine having at least one primary amine group.

Another aspect of the present invention relates to a process wherein hydrocarbon streams containing isomerizable conjugated diolefins are treated with a dispersion of an alkali(ne earth) metal in a hydrocarbon also containing an aliphatic amine having at least one primary amine group.

Preferably, the present invention relates to a process wherein cis- and/or cis/trans-piperylene(s) containing hydrocarbon streams are treated with a dispersion of an alkali(ne earth) metal in a hydrocarbon also containing an aliphatic amine having at least one primary amine group. It should be noted that allenic and/or alkynic impurities present in the isomerizable conjugated diolefins are also removed during the isomerization process which renders the process according to the present invention very flexible.

Conjugated diolefins which can be suitably upgraded according to the process according to the present invention comprise butadiene, isoprene, the piperylenes, 1,3-hexadiene and 1-vinylcyclohexene. The present process is of great interest for the upgrading of butadiene, in particular butadiene which has been obtained from the cracking of naphtha. The $C_4$-stream thus obtained contains apart from butadiene also butenes and butene and is commonly referred to as the BBB-steam. The main impurities normally present therein are vinylacetylene, butyne-1 and 1,2-butadiene. The level of impurities depends on the severity of the cracking operation and the possible working-up procedure(s) applied thereafter. It has been found that rather large amounts of impurities, e.g. 1,2-butadiene in an amount of up to 3% w can be easily removed without affecting the amount of valuable compounds in the BBB-stream. The main impurities in crude piperylene comprise pentyne-1, cyclopentadiene and in particular 1,1-dimethylallene. As stated hereinbefore, the purification of crude piperylene according to the process according to the invention has the intrinsic advantage of the simultaneous isomerization of the cis-isomer into the more valuable trans-isomer while removing the allenic and alkynic impurities which would affect the polymerization catalyst to be applied.

The upgrading according to the present invention is carried out in the presence of an amine according to the general formula $$R^1-NH_2 \qquad (I)$$

wherein $R^1$ represents an alkyl or aralkyl group or a group $(CR^2R^3)_nNR^4R^5$ wherein $R^2$, $R^3$ and $R^4$, which may be the same or different, each represent a hydrogen atom or a lower alkyl group, n represents an integer up to 8 and $R^5$ represents a hydrogen atom or a group $(CR^2R^3)_nNR^4R^5$ wherein $R^2$, $R^3$, $R^4$, $R^5$ and n are as defined hereinbefore or a group $R^6$ $(OCR^2R^3)_n$— wherein $R^6$ represents an alkyl, aryl or aralkyl group and $R^2$, $R^3$ and n are as defined hereinbefore. The upgrading is preferably carried out in the presence of amines according to the general formula I wherein $R^1$ represents an alkyl group of up to 16 carbon atoms or a group $(CR^2R^3)_nNH_2$ wherein $R^2$ and $R^3$, which may be the same or different, each represent a hydrogen atom or a lower alkyl group and n represents an integer of from 2 to 7, or a group $(CR^2R^3)_nNR^4R^5$ wherein $R^2$ and $R^3$, which may be the same or different, each represent a hydrogen atom or a lower alkyl group, $R^4$ represents hydrogen atom, n is an integer of from 2 to 7 and $R^5$ represents a group $(CR^2R^3)_nNR^4H$ wherein $R^2$, $R^3$, $R^4$ and n are as defined hereinbefore.

Examples of compounds according to the general formula I include primary mono-alkyl amines such as n-butylamine, sec-butylamine, n-pentylamine, n-hexylamine and cyclohexylamine. Examples of primary alkyldiamines include 1,2-diaminoethane, 1,2-diaminopropane, 1,3-diaminopropane, 1,2-diaminobutane, 1,4-diaminobutane, 1,5-diaminopentane, 1,6-diaminohexane and 1,4-diaminocyclohexane. Examples of polyamines containing at least one primary amine group include diethylenetriamine, triethylenetetramine, tetraethylenepentamine and the 1,1-dialkyldiethylenetriamines. Examples of oxygen-containing primary amines include 2-ethoxy ethylamine and 3-ethoxypropylamine. Preference is given to the primary monoalkylamines n-butylamine and n-hexylamine, the primary alkyl-diamines 1,2-diaminoethane, 1,2-diaminopropane and 1,3-diaminopropane and the polyamine diethylenetriamine. It is appreciated that the upgrading will benefit from a good compatibility of the various components in the reaction mixture. Mixtures of two or more compounds according to the general formula I can also be applied.

The process according to the present invention is carried out using a dispersion of an alkali(ne earth) metal. Dispersions of alkali(ne earth) metals, in particular sodium dispersions can easily be prepared by heating the solid alkali(ne earth) metal, in particular sodium in a suitable inert liquid until it has liquefied and subsequently mixing the two liquids vigorously, for example by stirring. If desired, a dispersant may be added to the mixture to accelerate the dispersion and to reduce the dimensions of the sodium particles. Examples of dispersants are fatty acids having a long carbon chain such as oleic acid. Higher alcohols and esters as well as some finely dispersed inert solids such as carbon can also be used. By cooling the mixture obtained down to temperatures below 98° C., the sodium forms solid particles which remain dispersed.

The liquid which constitutes the homogeneous phase can be any liquid which is essentially inert to the alkali(ne earth) metal applied, the conjugated diolefin to be treated and the polymerization catalyst to be used in the polymerization process envisaged. Exemplary are hydrocarbons, hydrocarbon mixtures or hydrocarbon fractions having a boiling range at atmospheric pressure from 50° to 500° C., for example gasoline, kerosene, gas oil and lubricating oil distillates or aromatic hydrocarbons such as benzene, toluene and the xylenes. Mineral lubricating oil fractions are preferred since the alkali(ne earth) metals, in particular sodium readily remain dispersed therein. The dispersions may contain up to about 50% w of alkali(ne earth) metal, preferably an amount in the range of from 10% w to 30% w.

The particle size of the finely dispersed alkali(ne earth) metal suspended in a liquid is not restricted to a sharply defined range. However, to facilitate shorter duration of the treatment and lower consumption of the alkali(ne earth) metal it is preferred to employ dispersions having alkali(ne earth) metal particles, in particular sodium particles, wherein half the number of sodium particles is smaller than 5 microns and most preferably smaller than 3 microns.

The process according to the present invention is normally carried out using an alkali(ne earth) metal dispersion in an amount sufficient to remove the allenic alkynic impurities present in the feed to be treated. Normally, dispersions of alkali(ne earth) metals are used which contain up to 20% w, preferably between 0.5% w and 5% w of alkali(ne earth) metal, calculated on the total amount of hydrocarbon of hydrocarbon stream to be upgraded.

The amount of amine according to the general formula I to be used is not critical and may vary between rather wide limits. It has been found that good results can be obtained using an alkali(ne earth) metal:amine gram atoms:molar ratio in the range between 15:1 and 1:10. Preference is given to the use of an alkali(ne earth) metal:primary amine ratio in the range of from 2:1 to 1:1 and an alkali(ne earth) metal:bis-primary amine molar ratio in the range of from 2:1 to 8:1.

The conjugated diolefin to be upgraded, may be in the gaseous or in the liquid phase or may be a mixture of the two phases. Preferably, the conjugated diolefin should be mixed in the liquid phase with a liquid soluble in the conjugated diolefin and containing suspended alkali(ne earth) metal, resulting in better contacting with the metal and more rapid removal of the unwanted compounds. Good results can be obtained when the amine to be used is added in the appropriate amount to a conjugated diolefin already containing a dispersion of an alkali(ne earth) metal. It is, of course, also possible to prepare a dispersion of an alkali(ne earth) metal and an appropriate amine which mixture is than added to the conjugated diolefin to be upgraded.

The process according to the present invention can be carried out conveniently at temperatures in the range of from 15° C. to 100° C. The removal of allenic and possibly alkynic impurities is preferably carried out at room temperature or slightly above, whereas the isomerization of the cis-isomers into the appropriate trans-isomers is preferably carried out at temperatures in the range between 35° C. and 60° C. It has been found that even at the higher temperatures polymerization of the conjugated dienes does not occur under the prevailing upgrading conditions.

It has been found that a very short contact time already allows for the removal of the allenic impurities which are notoriously difficult to remove compared with co-present alkynic impurities. Contact times as short as 15 minutes or even less are sufficient to remove the allenic impurities below the level of detection (<2 ppm). Prolonged contact times may be used but do not really contribute to the removal of impurities. Contact times much longer than one hour are not preferred because of the potential polymerization of the conjugated diolefins to be treated.

The process according to the present invention can be performed batchwise, semi-continuously or continuously. Preferably, the process according to the present invention is carried out continuously. Contacting of the conjugated dienes with the dispersion of an alkali(ne earth) metal also containing a compound according to the general formula I can be effected in one or more reactors, preferably provided with stirring equipment. When two or more reactors are applied, metallic and bound alkali(ne earth) metal can be separated from the conjugated diolefin stream discharged from the last reactor and recycled to the first reactor.

After treatment with the alkali(ne earth) metal, the stream thus treated contains metallic and bound alkali(ne earth) metal, the liquid in which the fresh alkali(ne earth) metal was dispersed and the conjugated diolefins enriched in the trans-isomer when appropriate. From this mixture, the conjugated diene has to be separated and it can then be used for further reactions such as polymerization. Normally, metallic and bound alkali(ne earth) metals are separated first, e.g. by means of filtration, centrifugation or decantation. Subsequently, the conjugated diolefin can be purified, if desired, by means of distillation; a conjugated diolefin fraction suitable for polymerization is obtained as the top product, while polymers, if any, and the liquid in which the fresh alkali(ne earth) metal was dispersed (where this had a boiling range or boiling point higher than that of the conjugated diene) are left in the residue.

The present invention further relates to a process for the polymerization of conjugated dienes, in particular 1,3-butadiene using as feedstock a hydrocarbon stream comprising conjugated diolefins which have been upgraded by a process according to the present invention. The present invention relates in particular to a process for the polymerization of 1,3-butadiene, if desired in the presence of co-polymerizable monomers, using a feedstock also containing butenes and butane which has been upgraded by a process according to the present invention as well as to polymers thus prepared. The polymerization can be carried out by methods known to those skilled in the art. For the polymerization, alkyllithium compounds in which the alkyl group contains of from 2 to 8 carbon atoms are preferred, such as sec-butyllithium, n-butyllithium and n-amyllithium. sec-Butyllithium is particularly preferred because it initiates the polymerization especially rapidly.

The invention will now be illustrated by means of the following Examples.

EXAMPLE I

A C$_4$-fraction was isolated by means of fractional distillation from a reaction product obtained by thermal cracking of a naphtha in the gas phase in the presence of steam. A typical Gas-Liquid Chromatgraphic (GLC) analysis of the crude BBB-fraction indicated as major components: 1,3-butadiene (45.6% w), butenes (49.1%) and butanes (2.1% w). Butyne-1 was present in an amount of 1350 ppm, vinylacetylene in an amount of 4560 ppm and 1,2-butadiene in an amount of 2210 ppm.

A typical sodium dispersion was prepared by vigorously stirring "SHELL TALPA" oil 30 ("SHELL TALPA" is a Registered Trade Mark for a lubricating oil, the oil 30 applied here had a viscosity of 9.0° E. and 1.82° E. at 50° and 100° C., respectively) with 10% w of metallic sodium at a temperature of 180° C.

The experiments described hereinafter were carried out in a 1 liter autoclave wherein 150 g of the BBB-fraction referred to hereinabove were mixed with the sodium dispersion referred to hereinabove in such amounts that 1% w sodium contents on crude BBB-fraction were obtained. Equimolar amounts with respect to sodium were added in the case of primary amines and halfmolar amounts when bis-primary amines were applied by introducing them through a rubber seal at the top of the autoclave while stirring the mixture at 25° C. During the experiments the gas phase in the reactor was submitted to GLC-analysis; samples were taken immediately after addition of the appropriate amines and at regular intervals.

The BBB-fraction was subjected to a treatment with the sodium dispersion as well as with the sodium dispersion also containing 1,2-propanediamine (sodium:amine ratio 1:2) at room temperature. The level of impurities remaining was determined by GLC-analysis after 45 minutes for the fraction treated only with the sodium dispersion and after 15 minutes for the fraction treated with the sodium dispersion in the presence of 1,2-diaminopropane. The results are given in Table A.

TABLE A

| Impurities (ppm) | Crude BBB | After sodium treatment | After sodium/amine treatment |
| --- | --- | --- | --- |
| 1,2-butadiene | 2210 | 2210 | <2 |
| vinylacetylene | 4560 | <2 | <2 |
| butyne-1 | 1350 | <2 | <2 |
| 1,3-butadiene (% w) | 45.6 | 45.6 | 45.7 |

EXAMPLE 2

To the BBB-fraction purified using 1,2-propanediamine as described in Example 1 was added a fresh amount of unwanted 1,2-butadiene (10,000 ppm on purified fraction). The level of impurities remaining was determined by GLC-analysis after 0.5, 15 and 30 minutes, respectively. The results are given in Table B.

TABLE B

| Impurities (ppm) | After 0.5 minutes | After 15 minutes | After 30 minutes |
| --- | --- | --- | --- |
| 1,2-butadiene | 7000 | 730 | <2 |
| vinylacetylene | <2 | <2 | <2 |
| butyne-1 | <2 | <2 | <2 |
| 1,3-butadiene (% w) | 45.6 | 45.7 | 45.6 |

EXAMPLE 3

The experiments described in Example 1 were repeated using various amines. The amines were added in 1:1 molar ratio to sodium for primary amines and 0.5:1 for bis-primary amines using a sodium dispersion of 1% w on crude BBB-fraction. For comparison, the results are also given when aniline (primary aromatic amine) and di-n-propyl amine (aliphatic secondary amine) are used. The results are given in Table C. The values in parentheses refer to the amount of impurities before treatment.

(3300 ppm) and cyclopentadiene (3000 ppm). The treatment was carried out at 25° C. using 1,2-propanedia-

TABLE C

| time (min.) | Amine | | | | | | | | | | | |
|---|---|---|---|---|---|---|---|---|---|---|---|---|
| | 1,2-Butadiene (2210) | | | | Butyne-1 (3150) | | | | Vinylacetylene (4560) | | | |
| | 1 | 15 | 30 | 60 | 1 | 15 | 30 | 60 | 1 | 15 | 30 | 60 |
| 1,2-Diaminoethane | 1640 | <2 | <2 | <2 | 300 | <2 | <2 | <2 | 2160 | <2 | <2 | <2 |
| 1,3-Diaminopropane | 1330 | <2 | <2 | <2 | 780 | <2 | <2 | <2 | 3190 | <2 | <2 | <2 |
| 1,6-Diaminohexane | 1380 | 860 | <2 | <2 | 820 | <2 | <2 | <2 | 3550 | <2 | <2 | <2 |
| Diethylenetriamine | 1430 | <2 | <2 | <2 | 880 | 130 | <2 | <2 | 3650 | 470 | <2 | <2 |
| n-Hexylamine | 890 | <2 | <2 | <2 | 260 | <2 | <2 | <2 | 1250 | 100 | 10 | <2 |
| n-Butylamine | 930 | <2 | <2 | <2 | 780 | <2 | <2 | <2 | 1160 | 10 | <2 | <2 |
| Aniline | 1840 | 1780 | 1700 | 1680 | 940 | 240 | <2 | <2 | 3680 | 400 | <2 | <2 |
| Di-n-propylamine | 1850 | 1600 | 1600 | 1490 | 1050 | 270 | <2 | <2 | 4050 | 20 | <2 | <2 |

EXAMPLE 4

Additional purity tests were performed to determine the selective polymerization of 1,3-butadiene in the purified BBB-fraction followed by polymer Gel Permeation Chromatgraphic (GPC)-analysis. Approximately 35 g BBB-samples were distilled from the reactor into 500 ml serum bottles, diluted with 200 ml cyclohexane, treated with 0.8 mmol sec-butyllithium and stirred overnight at 30° C. The molecular weight distributions of the obtained polybutadienes were compared with a reference sample prepared in cyclohexane by measurement of the respective GPC peakwidths at half-height. The results are given in Table D. It will be clear from this Table that when amines are used which are not in accordance with the general formula I (aniline, di-n-propylamine) broad molecular weight distributions are obtained, pointing to the presence of proton donating impurities such as 1,2-butadiene in the starting material.

TABLE D

| Amine used | GPC peak width (mm) |
|---|---|
| 1,2-ethanediamine | 9 |
| 1,2-propanediamine | 10 |
| 1,3-propanediamine | 9 |
| 1,6-hexanediamine | 10 |
| diethylenetriamine | 8 |
| n-hexylamine | 11 |
| n-butylamine | 9 |
| aniline | 26 |
| di-n-propylamine | 28 |
| reference (cyclohexane) | 9 |

EXAMPLE 5

An experiment as described in Example 1 was carried out using a crude piperylene stream which contained 70.2% w piperylenes (cis/trans ratio 0.44) and as main impurities 1,1-dimethylallene (1800 ppm), pentyne-1 (3300 ppm) and cyclopentadiene (3000 ppm). The treatment was carried out at 25° C. using 1,2-propanediamine and a sodium:amine ratio of 1:2. A similar experiment was carried out in the absence of amine. The results are given in Table E for samples taken after 30 and 60 minutes, respectively. The total amount of piperylenes was 69.5% w having a cis/trans ratio of 0.20 indicating that isomerization already occurs under the prevailing reaction conditions.

TABLE E

| Impurities (ppm) | | After sodium treatment | | After sodium/amine treatment | |
|---|---|---|---|---|---|
| | | 30 min. | 60 min. | 30 min. | 60 min. |
| 1,1-dimethylallene | 1800 | 1800 | 1800 | 1000 | 800 |
| pentyne-1 | 3300 | 3000 | 20 | <2 | <2 |
| cyclopentadiene | 3000 | 20 | <2 | 50 | <2 |

EXAMPLE 6

A number of purification/isomerization experiments was carried out using various amines. A control experiment in the absence of amine was also carried out. The starting material was a crude piperylene containing, according to GLC-analysis about 48% w of the trans-isomer and about 20.6% w of the cis-isomer and about 16% w of pentenes. The main impurities present in this feed were 1,1-dimethylallene, pentyne-1 and cyclopentadiene. The upgrading was carried out at 53° C. and the results are given in Table F, together with the particulars of the feed employed and the sodium:amine ratios applied. It will be clear from the data compiled in Table F that both the main impurities are reduced to below the level of (<2 ppm) and isomerization of cis-piperylene becomes increasingly significant, especially when diethylenetriamine is used as the compound according to the general formula I. Moreover, the total amount of piperylenes virtually remains constant during the experiments.

TABLE F

| components | amine | | | | | | | | | | | |
|---|---|---|---|---|---|---|---|---|---|---|---|---|
| | | | | | EDA | | | | HMDA | | | |
| | time | | | | | | | | | | | |
| | 0 | 15 | 30 | 60 | 0 | 15 | 30 | 60 | 0 | 15 | 30 | 60 |
| transpiperylene (%) | 48.0 | 47.7 | 47.7 | 48.0 | 48.0 | 48.0 | 49.8 | 49.7 | 47.8 | 49.4 | 50.1 | 51.1 |
| cis-piperylene (%) | 20.7 | 18.8 | 18.2 | 18.0 | 20.7 | 19.4 | 19.4 | 18.8 | 20.8 | 18.1 | 16.2 | 14.9 |
| 1,1-dimethylallene (ppm) | 1800 | 1800 | 1700 | 1310 | 1620 | <2 | <2 | <2 | 1600 | <2 | <2 | <2 |
| pentyne-1 (ppm) | 2090 | 1510 | 510 | <2 | 2090 | 390 | <2 | <2 | 1600 | 300 | 130 | <2 |
| cyclopentadiene (ppm) | 1690 | 1170 | 260 | <2 | 1690 | 290 | 40 | <2 | 1200 | 130 | <2 | <2 |
| sodium (g) | | | 0.9 | | | | 1.65 | | | | 1.65 | |
| amine (g) | | | — | | | | 0.75 EDA | | | | 2.80 HMDA | |
| —NH₂/Na ratio | | | — | | | | 0.35 | | | | 0.67 | |
| feed (g) | | | 90 | | | | 170 | | | | 170 | |

| | amine | |
|---|---|---|
| | PDA | DETA |

TABLE F-continued

|  | components | 0 | 15 | 30 | 60 | 0 | 15 | 30 | 60 |
|---|---|---|---|---|---|---|---|---|---|
|  |  |  |  |  | time |  |  |  |  |
|  | transpiperylene (%) | 49.9 | 51.2 | 51.4 | 55.4 | 48.0 | 52.0 | 54.5 | 57.4 |
|  | cis-piperylene (%) | 20.6 | 17.3 | 15.0 | 14.4 | 20.8 | 16.2 | 12.8 | 11.9 |
|  | 1,1-dimethylallene (ppm) | 1820 | 1000 | <2 | <2 | 1740 | 16 | <2 | <2 |
|  | pentyne-1 (ppm) | 1200 | 110 | 60 | <2 | 390 | 290 | <2 | <2 |
|  | cyclopentadiene (ppm) | 490 | 130 | 25 | <2 | 1200 | 160 | <2 | <2 |
|  | sodium (g) |  | 1.66 |  |  |  | 1.65 |  |  |
|  | amine (g) |  | 1.82 PDA |  |  |  | 1.25 DETA |  |  |
|  | —NH$_2$/Na ratio |  | 0.68 |  |  |  | 0.34 |  |  |
|  | feed (g) |  | 170 |  |  |  | 170 |  |  |

EDA = 1,2-diaminoethane
HMDA = 1,6-diaminohexane
PDA = 1,2-diaminopropane
DETA = diethylenetriamine

EXAMPLE 7

An experiment was carried out to demonstrate the isomerization of pure cis-piperylene into trans-piperylene using a sodium dispersion and diethylenetriamine (DETA) at a sodium:amine molar ratio of 6:1. The isomerization was performed at 45° C. The total feed was 50 g. For comparison the experiment was also carried out using only the sodium dispersion. The results are given in Table G. It should be noted that not only the degree of isomerization in the absence of an amine is considerably lower but that at the same time also a substantial amount of unwanted cyclopentene is co-producted (up to 9.4% w compared with less than 0.05% w using diethylenetriamine).

TABLE G

| isomer % w | treatment with sodium time (min.) | | | | treatment with sodium/DETA time (min.) | | | |
|---|---|---|---|---|---|---|---|---|
|  | 0 | 30 | 45* | 90* | 0 | 30 | 45 | 60 |
| cis-piperylene | 99.3 | 98.9 | 97.6 | 72.9 | 99.3 | 28.0 | 24.5 | 18.2 |
| trans-piperylene | 0.3 | 0.8 | 2.0 | 17.8 | 0.5 | 69.9 | 73.0 | 78.7 |

*gel formation

I claim:

1. Process for the upgrading of a hydrocarbon mixture containing conjugated diolefin which comprises contacting said mixture with a dispersion of at least one metal selected from alkali and alkaline earth metals in the presence of an aliphatic amine according to the general formula $$R^1—NH_2 \qquad (I)$$

wherein $R^1$ represents an alkyl group of up to 16 carbon atoms or a group $(CR^2R^3)_nNR^4R^5$ wherein $R^2$, $R^3$ and $R^4$, which may be the same or different, each represent a hydrogen atom or a lower alkyl group, n represents an integer up to 8 and $R^5$ represents a hydrogen atom or a group $(CR^2R^3)_nNR^4H$ wherein $R^2$, $R^3$, $R^4$ and n are as defined hereinbefore.

2. Process according to claim 1, wherein said hydrocarbon feed mixture contains additional compounds selected from allenes and acetylenic compounds are treated with a dispersion of an alkali(ne earth) metal in a hydrocarbon having a boiling temperature at atmospheric pressure in the range from 50°–500° C. also containing an aliphatic amine having at least one primary amine group.

3. Process according to claim 1, wherein said hydrocarbon feed mixture contains at least one $C_4$–$C_8$ conjugated diolefin.

4. Process according to claim 1, wherein said hydrocarbon feed mixture contains at least one isomerizable conjugated diolefin.

5. Process according to claim 1, wherein said feed mixtures contains at least one of cis- and cis-trans piperylene(s).

6. Process according to claim 1, wherein said aliphatic amine is a mono- or diaminoalkane or diethylenetriamine.

7. Process according to claim 6, wherein said amine is selected from at least one of the group consisting of n-butylamine, n-hexylamine, 1,2-diaminoethane, 1,2-diaminopropane, 1,3-diaminopropane and diethylenetriamine.

8. Process according to claim 1, wherein during said contacting the dispersion of metal contains up to 20% w, of said alkali as alkaline (earth) metal, calculated on the amount of hydrocarbon feed mixture to be upgraded.

9. Process according to claim 1, wherein the gram atoms:molar ratio of metal:primary amine is in the range between 15:1 and 1:10.

10. Process according to claim 1, wherein said contacting is carried out at a temperature between 15° C. and 100° C.

11. Process according to claim 1, wherein said contacting is carried out at a temperature in the range of from 35° to 60° C.

* * * * *